US012697090B2

(12) United States Patent
Bae et al.

(10) Patent No.: US 12,697,090 B2
(45) Date of Patent: Aug. 4, 2026

(54) METHOD AND DEVICE FOR QUANTITATIVE IMAGING IN MEDICAL ULTRASOUND

(71) Applicant: KOREA ADVANCED INSTITUTE OF SCIENCE AND TECHNOLOGY, Daejeon (KR)

(72) Inventors: Hyeon-Min Bae, Daejeon (KR); Seokhwan Oh, Daejeon (KR); Myeong Gee Kim, Daejeon (KR); Youngmin Kim, Daejeon (KR); Guil Jung, Daejeon (KR)

(73) Assignee: BARRELEYE INC, Daejeon (KR)

( * ) Notice: Subject to any disclaimer, the term of this patent is extended or adjusted under 35 U.S.C. 154(b) by 302 days.

(21) Appl. No.: 18/578,815

(22) PCT Filed: Jul. 1, 2022

(86) PCT No.: PCT/KR2022/009522
§ 371 (c)(1),
(2) Date: Jan. 12, 2024

(87) PCT Pub. No.: WO2023/287083
PCT Pub. Date: Jan. 19, 2023

(65) Prior Publication Data
US 2024/0382173 A1 Nov. 21, 2024

(30) Foreign Application Priority Data

Jul. 14, 2021 (KR) ......................... 10-2021-0091918
Mar. 17, 2022 (KR) ......................... 10-2022-0033573

(51) Int. Cl.
*A61B 8/08* (2006.01)
*A61B 8/00* (2006.01)
(Continued)

(52) U.S. Cl.
CPC ................ *A61B 8/085* (2013.01); *A61B 8/14* (2013.01); *A61B 8/5246* (2013.01); *G16H 30/40* (2018.01);
(Continued)

(58) Field of Classification Search
CPC ......... A61B 8/085; A61B 8/14; A61B 8/5246; A61B 8/461; A61B 8/485; A61B 8/5207;
(Continued)

(56) References Cited

U.S. PATENT DOCUMENTS

2014/0364734 A1    12/2014  Huang
2018/0185005 A1    7/2018  Sandhu et al.
(Continued)

FOREIGN PATENT DOCUMENTS

JP          2012-239546          12/2012
JP          6457157              1/2019
(Continued)

OTHER PUBLICATIONS

Myeong Gee Kim et al., "Quantitative imaging with a single probe in abdominal ultrasound", Medical Imaging 2023: Ultrasonic Imaging and Tomography 12470, 56-62, Apr. 2023 (abstract only).
(Continued)

*Primary Examiner* — Amelie R Davis
(74) *Attorney, Agent, or Firm* — LEX IP MEISTER, PLLC

(57) ABSTRACT

Disclosed is a method of an imaging device operated by at least one processor. The method includes: receiving pulse-echo data obtained from a tissue; and outputting a quantitative image of an objective variable using a B-mode image generated from the pulse-echo data, and a quantitative style feature extracted from the pulse-echo data.

19 Claims, 10 Drawing Sheets

(51) Int. Cl.
   *A61B 8/14*      (2006.01)
   *G16H 30/40*      (2018.01)
(52) U.S. Cl.
   CPC ............... *A61B 8/461* (2013.01); *A61B 8/485* (2013.01); *A61B 8/5207* (2013.01); *A61B 8/5223* (2013.01)
(58) Field of Classification Search
   CPC ...... A61B 8/5223; G16H 30/40; G16H 50/20; G06N 3/08; G06T 7/00
   See application file for complete search history.

(56) References Cited

U.S. PATENT DOCUMENTS

| | | | | |
|---|---|---|---|---|
| 2019/0336108 A1* | 11/2019 | Hope Simpson | ..... | G06T 7/0012 |
| 2019/0339371 A1* | 11/2019 | Dhatt | ................... | A61B 8/5215 |
| 2021/0212647 A1* | 7/2021 | Zheng | ................... | G06T 7/0012 |

FOREIGN PATENT DOCUMENTS

| | | |
|---|---|---|
| JP | 2021-133123 | 9/2021 |
| KR | 10-2007-0069322 | 7/2007 |
| KR | 10-2013-0080640 | 7/2013 |
| KR | 10-2067340 | 1/2020 |
| KR | 10-2021-0075831 | 6/2021 |
| WO | 2020-254159 | 12/2020 |

OTHER PUBLICATIONS

SeokHwan Oh et al., "A learned representation for multi-variable ultrasonic lesion quantification", 2021 IEEE 18th International Symposium on Biomedical Imaging (ISBI), 1177-1181, Apr. 13-16, 2021 (abstract only).
Myeong-Gee Kim et al., "Robust Single-Probe Quantitative Ultrasonic Imaging System With a Target-Aware Deep Neural Network", IEEE Trans Biomed Eng., vol. 68, No. 12, 3737-3747, Nov. 1, 20219 (abstract only).
Sanabria, Sergio J. et al., "Speed-of-Sound Imaging Based on Reflector Delineation", IEEE Transactions on Biomedical Engineering 66(7), Jul. 2019.
Cuiping Li et al., "In Vivo Breast Sound-Speed Imaging With Ultrasound Tomography", Ultrasound in Med. & Biol., vol. 35, No. 10, pp. 1615-1628, 2009.
SeokHwan Oh et al., "A Neural Framework for Multi-variable Lesion Quantification Through B-Mode Style Transfer", M. de Bruijne et al. (Eds.): MICCAI 2021, LNCS 12906, pp. 222-231, 2021. (Sep. 21, 2021).

* cited by examiner

FIG. 1

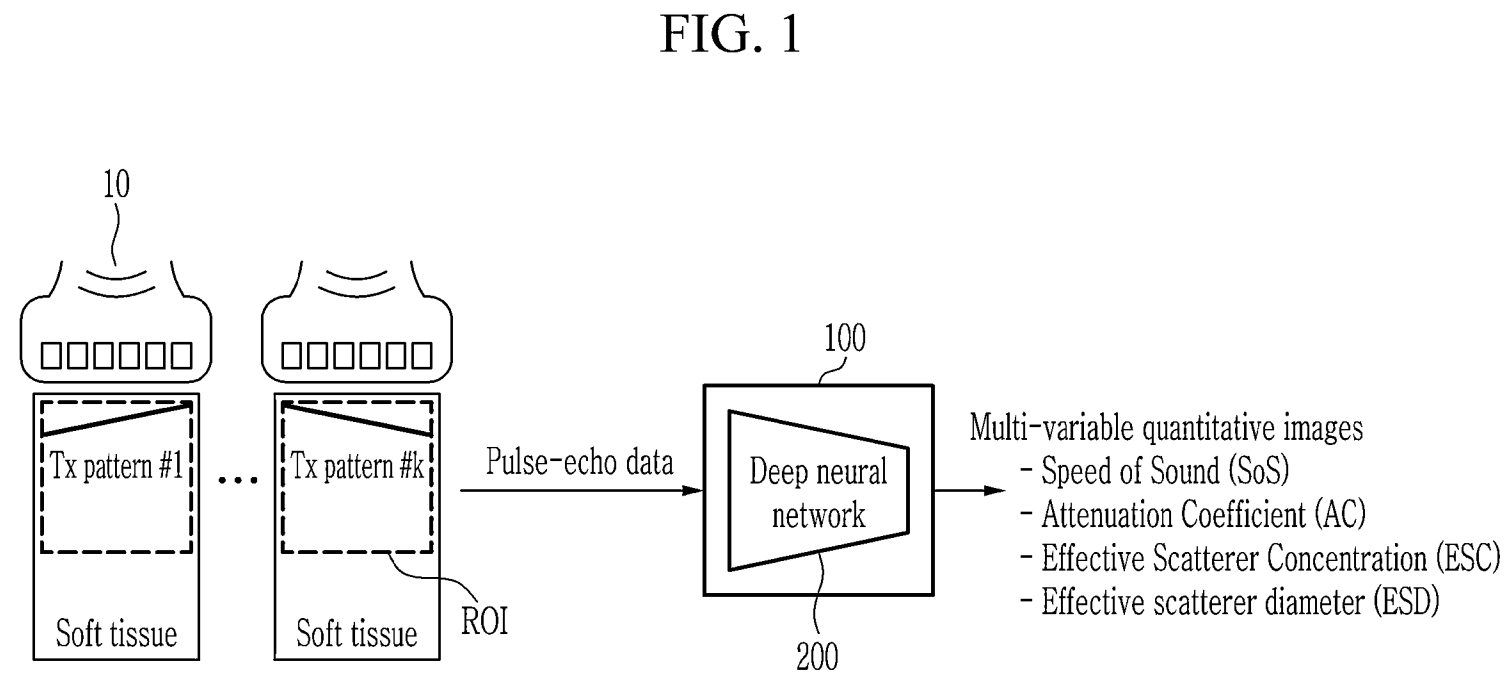

Multi-variable quantitative images
- Speed of Sound (SoS)
- Attenuation Coefficient (AC)
- Effective Scatterer Concentration (ESC)
- Effective scatterer diameter (ESD)

Deep neural network

100

200

Pulse-echo data

ROI

Tx pattern #k

Soft tissue

Tx pattern #1

Soft tissue

230 multi-resolution Content features $C_{16\times16}$    321

Figure 4:
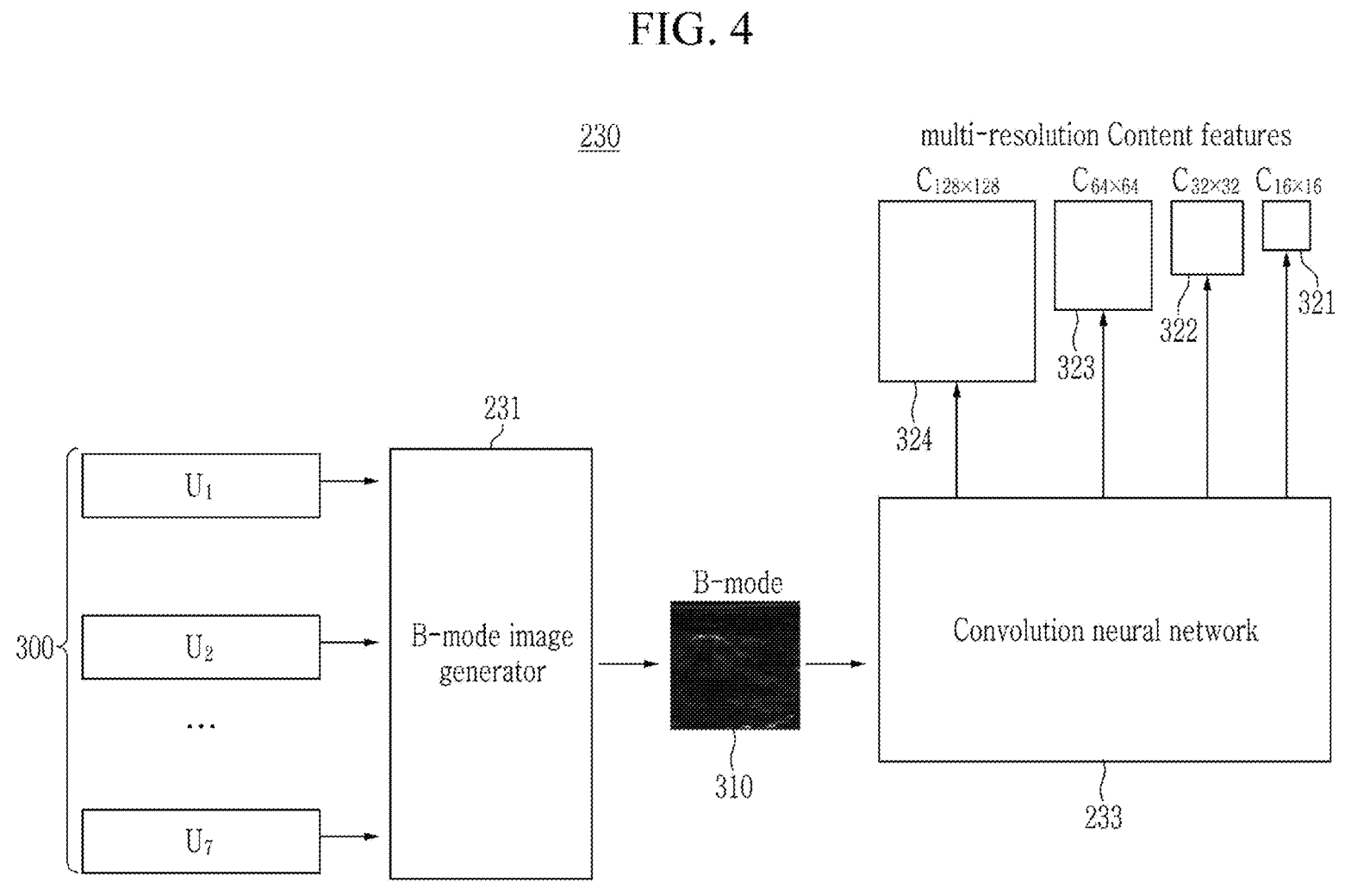

$C_{32\times32}$    322

$C_{64\times64}$    323

$C_{128\times128}$    324

Convolution neural network    233

B-mode    310

B-mode image generator    231

$U_1$ $U_2$ $\vdots$ $U_7$

300

METHOD AND DEVICE FOR QUANTITATIVE IMAGING IN MEDICAL ULTRASOUND

TECHNICAL FIELD

The present disclosure relates to ultrasonic quantification technology.

BACKGROUND ART

Cancer is difficult to detect early, requiring periodic diagnosis, and the size and characteristics of lesions must be continuously monitored. Representative imaging equipment for this includes X-ray, magnetic resonance imaging (MRI), computed tomography (CT), and ultrasound. While the X-ray, the MRI, and the CT have the disadvantages of risk of radiation exposure, long measurement time, and high cost, the ultrasound imaging equipment is safe, relatively inexpensive, and provides real-time images, allowing users to monitor the lesion in real time and obtain the desired image.

Currently, the most commercialized ultrasound imaging equipment is a B-mode (Brightness mode) imaging system. A B-mode imaging method is a method of determining the location and size of an object through the time and intensity at which an ultrasound is reflected from the surface of the object and returned. In this method, since the lesion is searched in real time, a user can efficiently obtain the desired image while monitoring the lesion in real time, and this method is safe and relatively inexpensive, and can be easily accessed. However, this method has a disadvantage of not maintaining consistent image quality depending on the user's skill level and not being able to image quantitative characteristics. In other words, because the B-mode technique provides only morphological information of the tissue, sensitivity and specificity may be low in differential diagnosis for distinguishing between benign and malignant tumors based on histological characteristics.

Pathological changes in tissue cause structural changes in cells, and this involves imaging changes in ultrasound properties in the tissue and representative examples include elastography and ultrasound computed tomography (USCT). The elastography can quantitatively image tissue elasticity and stiffness, but require additional dedicated devices and consume a lot of energy. Therefore, the elastography can only be applied to expensive ultrasound equipment and have a low frame rate, making them unsuitable for imaging dynamically shifting tissues. The USCT can obtain high-resolution quantitative images, but an ultrasound sensor must surround the object, so the ultrasound sensor is limited to mammography and has limitations in measuring various organs. The USCT takes minutes for imaging, so real-time movement cannot be seen, and the size of the system is so large that it is impossible to move.

Recently, there have been attempts to extract quantitative variables from pulse-echo data, but there are limitations in reconstructing complex tissue structures compared to B-mode images.

DISCLOSURE

Technical Problem

The present disclosure attempts to provide a method and a device for imaging quantitative features for various variables of a tissue from pulse-echo data by applying quantitative style information to a B-mode image The present disclosure attempts to provide a neural network that reconstructs quantitative information on variables including Speed of Sound (SoS), Attenuation Coefficient (AC), Effective Scatterer Concentration (ESC), and Effective Scatterer Diameter (ESD) by using pulse-echo data acquired in the tissue through a single ultrasound probe.

Technical Solution

An exemplary embodiment of the present disclosure provides a method for operation by an imaging device operated by at least one processor. The method includes: receiving pulse-echo data obtained from a tissue; and outputting a quantitative image of an objective variable using a B-mode image generated from the pulse-echo data, and a quantitative style feature extracted from the pulse-echo data.

The pulse-echo data may be radio frequency (RF) data in which ultrasound signals incident on the tissue with different beam patterns are reflected on the tissue, and returned.

The objective variable may include at least one of Speed of Sound (SoS), Attenuation Coefficient (AC), Effective Scatterer Concentration (ESC), and effective scatterer diameter (ESD).

The outputting the quantitative image of the objective variable may include: style-transferring content features of the B-mode image into quantitative images by using the quantitative styling feature; and reconstructing the quantitative images generated by style transfer to output the quantitative image of the objective variable.

The outputting the quantitative image of the objective variable may include: extracting the quantitative style feature of the objective variable included in the pulse-echo data, generating the B-mode image from the pulse-echo data, and extracting the content features of the B-mode image, and reconstructing the quantitative image of the objective variable by applying the quantitative style feature of the objective variable on the content features of the B-mode image.

The extracting the quantitative style feature of the objective variable may include extracting the quantitative style feature of a selected objective variable from the pulse-echo data, through conditional encoding according to the selected objective variable.

The extracting the content features of the B-mode image may include extracting the content features including geometric information of the tissue in the B-mode image.

The extracting the content features of the B-mode image may include extracting multi-resolution content features.

The reconstructing the quantitative image of the objective variable may include generating a high-resolution quantitative image by using parallel multi-resolution subnetworks.

Another exemplary embodiment of the present disclosure provides a method for operation by an imaging device operated by at least one processor. The method includes: extracting a quantitative style feature of an objective variable included in pulse-echo data by using a style encoder; generating a B-mode image from the pulse-echo data, and extracting content features of the B-mode image, by using a B-mode encoder; and reconstructing a quantitative image of the objective variable by applying the quantitative style feature of the objective variable on content features of the B-mode image, by using a decoder.

The style encoder may be a neural network trained to extract a quantitative style feature of a selected objective variable from the pulse-echo data through conditional encoding according to the selected objective variable.

The B-mode encoder may be a neural network trained to generate a B-mode image from the pulse-echo data, and extract the content features including geometric information from the B-mode image.

The decoder may be a neural network trained to receive content features extracted from the B-mode encoder, style-transfer the content features of the B-mode image into quantitative images by using the quantitative styling feature, and reconstruct the quantitative images generated by the style transfer to output the quantitative image of the objective variable.

The decoder may be a neural network with a structure of parallel multi-resolution subnetworks.

The objective variable may include at least one of Speed of Sound (SoS), Attenuation Coefficient (AC), Effective Scatterer Concentration (ESC), and effective scatterer diameter (ESD).

Still exemplary embodiment of the present disclosure provides an imaging device. The imaging device includes: a memory storing instructions; and a processor executing the instructions to receive pulse-echo data obtained from a tissue; and output a quantitative image of an objective variable using a B-mode image generated from the pulse-echo data, and a quantitative style feature extracted from the pulse-echo data.

The processor may be configured to style-transfer content features of the B-mode image into quantitative images by using the quantitative styling feature, and reconstruct the quantitative images generated by style transfer to output the quantitative image of the objective variable.

The processor may be configured to extract the quantitative style feature of the objective variable included in the pulse-echo data, generates the B-mode image from the pulse-echo data, and extract the content features of the B-mode image, and reconstruct the quantitative image of the objective variable by applying the quantitative style feature of the objective variable on the content features of the B-mode image.

The processor may be configured to extract the quantitative style feature of a selected objective variable from the pulse-echo data, through conditional encoding according to the selected objective variable.

The objective variable may include at least one of Speed of Sound (SoS), Attenuation Coefficient (AC), Effective Scatterer Concentration (ESC), and effective scatterer diameter (ESD).

Advantageous Effects

According to an exemplary embodiment, multi-variable quantitative images can be reconstructed in real time from ultrasound data of a tissue through a single neural network.

According to an exemplary embodiment, by applying quantitative style information to a B-mode image that provides accurate tissue structure information, various types of clinically important quantitative information can be provided simultaneously and high sensitivity and specificity sufficient to identify and classify cancer lesions can be provided.

According to an exemplary embodiment, since an ultrasound probe and an imaging device for B-mode imaging can be used as they are, image photographing is simple and various organs that can be measured with existing ultrasound imaging equipment can be measured.

According to an exemplary embodiment, a high-quality quantitative image can be reconstructed regardless of the user's skill level using a single ultrasound probe.

DESCRIPTION OF THE DRAWINGS

FIG. 1 is a diagram for conceptually describing a multi-variable quantitative imaging device according to an exemplary embodiment.

FIG. 4 illustrates a network structure of a B-mode encoder according to an exemplary embodiment.

MODE FOR INVENTION

Figure 2:
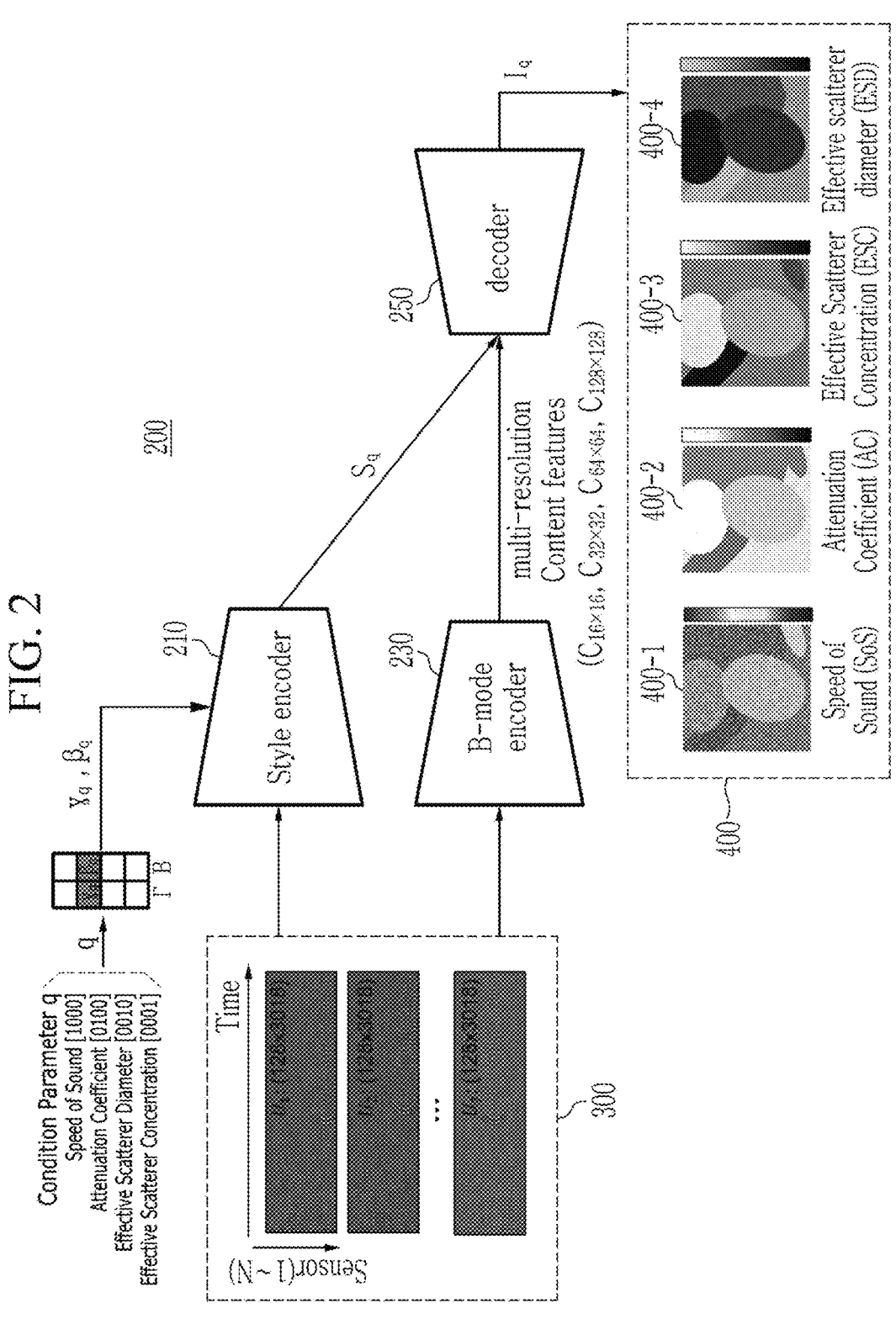
FIG. 2 is a conceptual view of a neural network according to an exemplary embodiment.

In the following detailed description, only certain exemplary embodiments of the present disclosure have been shown and described, simply by way of illustration. However, the present disclosure can be variously implemented and is not limited to the following exemplary embodiments. The drawings and description are to be regarded as illustrative in nature and not restrictive. Like reference numerals designate like elements throughout the specification.

Throughout the specification, unless explicitly described to the contrary, the word "comprise", and variations such as "comprises" or "comprising", will be understood to imply the inclusion of stated elements but not the exclusion of any other elements. In addition, the terms "-er", "-or", and "module" described in the specification mean units for processing at least one function and operation, and can be implemented by hardware components or software components, and combinations thereof.

A neural network of the present disclosure is an artificial intelligence model that learns at least one task, and may be implemented as software/program executed in a computing device. The program is stored on a non-transitory storage media and includes instructions written to execute operations of the present disclosure by a processor. The program may be downloaded through a network or sold in a product form.

FIG. 1 is a diagram for conceptually describing a multi-variable quantitative imaging device according to an exemplary embodiment.

Referring to FIG. 1, a multi-variable quantitative imaging device (simply referred to as 'imaging device') 100 as a computing device operated by at least one processor receives pulse-echo data obtained from a tissue through a single ultrasound probe 10, and extracts quantitative information of the tissue by using a neural network 200. The imaging device 100 is equipped with a computer program for operations described in the present disclosure, and the computer program is executed by a processor.

The imaging device 100 may complexly generate multi-variable quantitative images of the tissue using the neural network 200 that extracts quantitative features of the tissue from the pulse-echo data. Here, the imaging device 100 may reconstruct quantitative variables of the tissue, such as Speed of Sound (SoS), Attenuation Coefficient (AC), Effective Scatterer Concentration (ESC) which represents the density distribution within the tissue, and effective scatterer diameter (ESD), which indicates the size of inner cells in the tissue, etc. The neural network 200 may be called B-mode-to-Quantitative Imaging Network (BQI-Net).

Meanwhile, each of the Speed of Sound (SoS), the Attenuation Coefficient (AC), the Effective Scatterer Concentration (ESC), and the effective scatterer diameter (ESD) is known as biomarkers for lesion extraction and is closely related to the biomechanical properties of tissue. Therefore, the more variables used, the more comprehensive analysis of lesions can be performed, thereby increasing diagnostic sensitivity and specificity. However, because each variable has a distinct effect on ultrasound propagation, it is not easy to simultaneously reconstruct multiple variables from pulse-echo data.

To solve this problem, the neural network 200 applies quantitative style information to B-mode images that provide accurate structural information, thereby simultaneously providing various types of clinically important quantitative information from the pulse-echo data. The neural network 200 may perform conditional quantitative style encoding to efficiently generate quantitative images.

The neural network 200 as an artificial intelligence model that learns at least one task may be implemented as software/program executed in a computing device.

The ultrasound probe 10 has N (e.g., 128) ultrasound sensors arranged, and the sensors may be implemented as piezoelectrical elements. Additionally, the ultrasound probe 10 may be a phased array probe that generates an ultrasound signal by applying an electrical signal to each piezoelectric element at regular time intervals. For reference, the ultrasound probe 10 may be a typical B-mode imaging probe.

The ultrasound probe 10 may sequentially radiate ultrasound signals of different beam patterns (Tx pattern #1 to #k) to the tissue and acquire radio frequency (RF) data reflected from the tissue and returned. RF data obtained from multiple beam patterns are collected and simply referred to as pulse-echo data. The pulse-echo data may be called beamformed ultrasound data. The pulse-echo data is, for example, RF data obtained from seven different beam patterns $\theta_1$ to $\theta_7$, and the different beam patterns have incident angles of, for example, $-15°$, $-10°$, $-5°$, $0°$, $5°$, $10°$, and $15°$. A region of interest (ROI) may be set considering a transducer width of the ultrasound probe 10. For example, the ROI may be set to 40 mm×40 mm.

Meanwhile, the pulse-echo data obtained from the ultrasound probe 10 includes delay time information for receiving the reflected ultrasonic signal for each sensor of the ultrasound probe 10. The pulse-echo data may be expressed as an image representing delay time information for each sensor.

FIG. 2 is a conceptual view of a neural network according to an exemplary embodiment.

Referring to FIG. 2, the neural network 200 reconstructs quantitative information for objective variables (the Speed of Sound, the Attenuation Coefficient, the Effective Scatterer Concentration, and the effective scatterer diameter, etc.) from the pulse-echo data 300 and outputs a quantitative image 400. Here, the neural network 200 applies quantitative style information to B-mode images that provide accurate structural information, thereby simultaneously providing various types of clinically important quantitative information from the pulse-echo data 300.

The pulse-echo data 300 is RF data that is reflected back from the tissue by sequentially radiating ultrasound signals in various beam patterns. For example, the pulse-echo data 300 may be RF data $U_1$ to $U_7$ obtained from seven different beam patterns $\theta_1$ to $\theta_7$. The pulse-echo data U includes information on a time of receiving ultrasound echoes from the sensors of the ultrasound probe 10.

When the objective variable is the Speed of Sound (SoS), the neural network 200 may reconstruct a SoS image 400-1. When the objective variable is the Attenuation Coefficient (AC), the neural network 200 may reconstruct an AC image 400-2. When the objective variable is the Effective Scatterer Concentration (ESC), the neural network 200 may reconstruct an ESC image 400-3. When the objective variable is the effective scatterer diameter (ESD), the neural network 200 may reconstruct an ESD image 400-4. Besides, the neural network 200 may output images in which quantitative information of multiple objective variables are combined.

The neural network 200 may include a style encoder 210 that extracts a quantitative style feature $S_q$ of an objective variable q, and a B-mode encoder 230 that extracts a content feature of a B-mode image, and a decoder 250 that reconstructs a quantitative image $I_q$ by converting the content feature into a style of the objective variable.

The style encoder 210 selectively extracts quantitative style features $S_q$ ($S_{SOS}$, $S_{AC}$, $S_{ESC}$, and $S_{ESD}$) of the objective variable q included in the pulse-echo data 300. The style encoder 210 may be reconfigured to perform various tasks simply by adjusting a bias of the model. For example, the style encoder 210 performs conditional instance normalization (CIN) to extract a quantitative style feature corresponding to the objective variable. At this time, the quantitative style feature $S_q$ may be expressed with a spatial resolution $R^{16×16×512}$.

The style encoder 210 changes network parameters according to the objective variable to extract quantitative the quantitative style feature corresponding to the objective variable from the pulse-echo data 300. Specifically, the style encoder 210 may normalize an input x by transferring (scaling and shifting) the input x, using $\gamma_q$ and $\beta_q$ selected from the ΓB matrix, according to the objective variable q. Each objective variable q may be expressed as a one-hot vector, and used to extract the normalization parameters of the corresponding objective variable from the ΓB matrix. $\gamma_q$ is the scaling value for the objective variable q, and $\beta_q$ is the shift value for the objective variable q.

The style encoder 210 may normalize (CIN) the input x using normalization parameters $\gamma_q$ and $\beta_q$ selected according to the objective variable q, as shown in Equation 1. In Equation 1, $\mu(x)$ and $\sigma(x)$ are a mean and a standard deviation of the input x.

$$CIN(x, q) = \gamma_q \times \frac{x - \mu(x)}{\sigma(x)} + \beta_q \qquad \text{(Equation 1)}$$

The B-mode encoder 230 extracts a content feature of the B-mode image generated from the pulse-echo data 300. The B-mode encoder 230 may extract geometric information of the tissue from the B-mode image. The B-mode image may be generated by applying Delay and Sum (DAS) and time gain compensation (TGC) to the pulse-echo data 300. The B-mode encoder 230 may extract semantic contents about a tissue structure from a B-mode image including structure information of the tissue. At this time, the B-mode encoder 230 may extract multi-resolution content features (e.g., $C_{16\times16}$, $C_{32\times32}$, $C_{64\times64}$, and $C_{128\times128}$) from the B-mode image and provide the content features to the decoder 250.

The decoder 250 receives the quantitative style feature $S_q$ of the objective variable q extracted from the style encoder 210 and the content feature of the B-mode image extracted from the B-mode encoder 230. The decoder 250 reflects the quantitative styling feature $S_q$ of the target variable q in the content features of the B-mode image and reconstructs the quantitative image $I_q$ of the objective variable q. The quantitative image $I_q$ may be the SoS image 400-1, the AC image 400-2, the ESC image 400-3, and the ESD image 400-4.

The decoder 250 may gradually synthesize multi-resolution content features output from the B-mode encoder 230 to reconstruct a detailed quantitative image. The decoder 250 may have a network structure capable of reconstructing a high-resolution quantitative image, and for example, generate the high-resolution quantitative image by using High-Resolution Network (HRNet) based parallel multi-resolution subnetworks. At this time, the decoder 250 transfers the content feature c into quantitative images reflecting the quantitative styling feature $S_q$ through a style transfer, and gradually synthesizes the style-transfered quantitative images through sequential convolution layers to reconstruct high-resolution quantitative images. The style transfer may perform spatially adaptive demodulation (SPADE). The decoder 250 may spatially adaptively transfer each content feature c through the quantitative styling feature $S_q$, as shown in Equation 2.

$$SPADE(c, S_q) = Y_{x,y,ch}(S_q) \times \frac{c - \mu_{ch}(c)}{\sigma_{ch}(c)} + \beta_{x,y,ch}(S_q) \qquad \text{(Equation 2)}$$

In Equation 2, the B-mode content feature c is channel-wise transferred with quantitative styling feature $S_q$. For example, when the quantitative styling feature $S_q$ is expressed as $R^{16\times16\times512}$, a content feature c having a size of 16×16 may be transferred into a quantitative image having 512 channels by the quantitative styling feature $S_q$. $\mu_{ch}(c)$ and $\sigma_{ch}(c)$ are a mean and a standard deviation for each channel of an input c. $\gamma_{x,y,ch}(S_q)$ and $\beta_{x,y,ch}(S_q)$ as transfer parameters may be learned parameters generated by a 2D convolution. The transfer parameters may be adaptively derived according to a spatial relationship between the content feature c and the quantitative styling feature $S_q$. Spatial adaptive transfer may provide accurate interpretation of a correlation between quantitative information and a lesion location.

Training data of the neural network 200 may include pulse-echo data obtained from simulation phantoms and may be collected using an ultrasound simulation tool (e.g., k-wave toolbox of Matlab). For example, the neural network 200 may be trained through 19.5 k simulation phantoms. Here, 17.5 k phantoms may be used for training, 1.5 k phantoms may be used for validation, and 1.5 k phantoms may be used for testing.

For example, in the simulation phantom, organs and lesions may be expressed by placing 0 to 5 ellipses with a radius of 2 to 30 mm at random positions on a 50×50 mm background. Each lesion and background has a biomechanical property set to include general soft tissue properties. For example, the Speed of Sound (SoS) may be 1400 m/s to 1700 m/s, the Attenuation Coefficient (AC) may be 0 dB/MHz/cm to 1.5 dB/MHz/cm, the Effective Scatterer Concentration (ESC) may be 25 to 150 μm, the effective scatterer diameter (ESD) may be is 0 to 10/wavelength $(wav)^2$, and a background density may be set to 0.9 kg/m to 1.1 kg/m³.

The training device may train the neural network 200 to reconstruct a quantitative image of the objective variable q from pulse-echo data obtained through the simulation phantom. For convenience, it is described that the imaging device 100 trains the neural network 200, but the neural network 200 may be trained by a separate device and then installed in the imaging device 100.

An objective function G* used for training the neural network 200 may be defined as a loss function such as Equation 3. The neural network 200 may perform training of minimizing restoration loss using the objective function G*.

$$G^* = \operatorname*{argmin}_{G} \mathbb{E}_{U,Y}\left[\|Y_q - G(U, q)\|^2\right] + L_{SUB} + \lambda L_2 \qquad \text{(Equation 3)}$$

$$L_{SUB} = \mathbb{E}_{U,Y_{q,R}} \sum_{R} \|Y_{q,R} - G_R(U, q)\|^2, \ L_2 = \sum_{i=1} w_i^2 \qquad \text{(Equation 4)}$$

In Equation 3, $Y_q$ is a ground truth quantitative image for the objective variable q. G(U, q) is an output value of the neural network 200 according to the pulse-echo data U and the objective variable q. $Y_{q,R}$ is a downsampling image of $Y_q$ with spatial resolution $\{R^{16\times16}, R^{32\times32}, R^{64\times64}, R^{128\times128}\} \in R$.

The objective function G* is a function that minimizes a difference between the output value G(U,q) inferred from the pulse-echo data U and the ground truth $Y_q$ for the objective variable q. At this time, the objective function G* may include $L_{SUB}$, which regularizes the subnetwork of the decoder 250, as shown in Equation 4. $L_{SUB}$ is a term that regulates a subnetwork that gradually synthesizes quantitative images $I_{q,R}$ for each resolution based on the difference between the inferred value $G_R(U,q)$ inferred for each resolution and the ground truth $Y_{q,R}$ of the corresponding resolution. $L_2$ is a term to avoid overfitting by regularizing a weight $w_i$ of the neural network.

Figure 3:
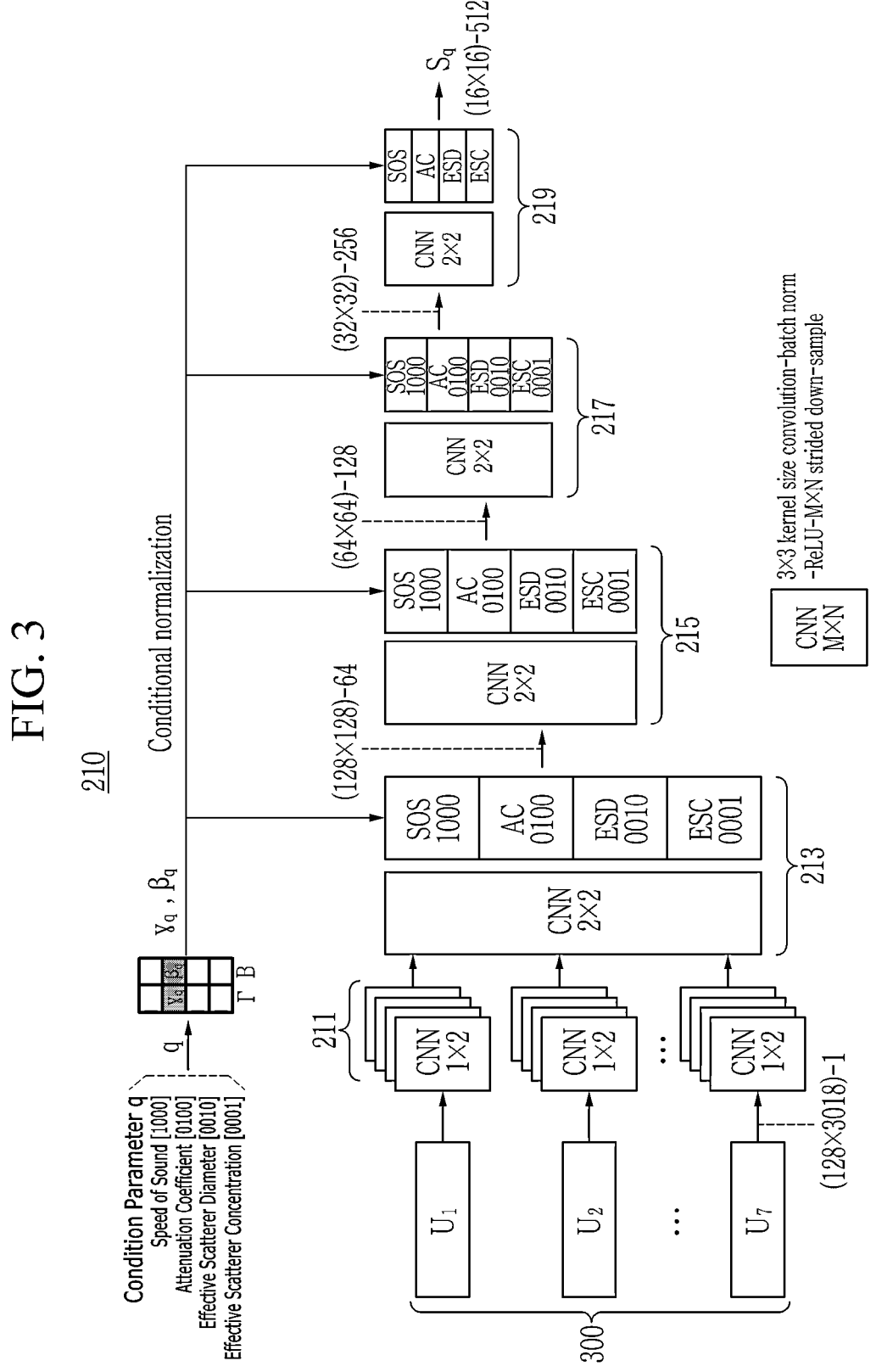
FIG. 3 illustrates a network structure of a style encoder according to an exemplary embodiment.
Figure 5:
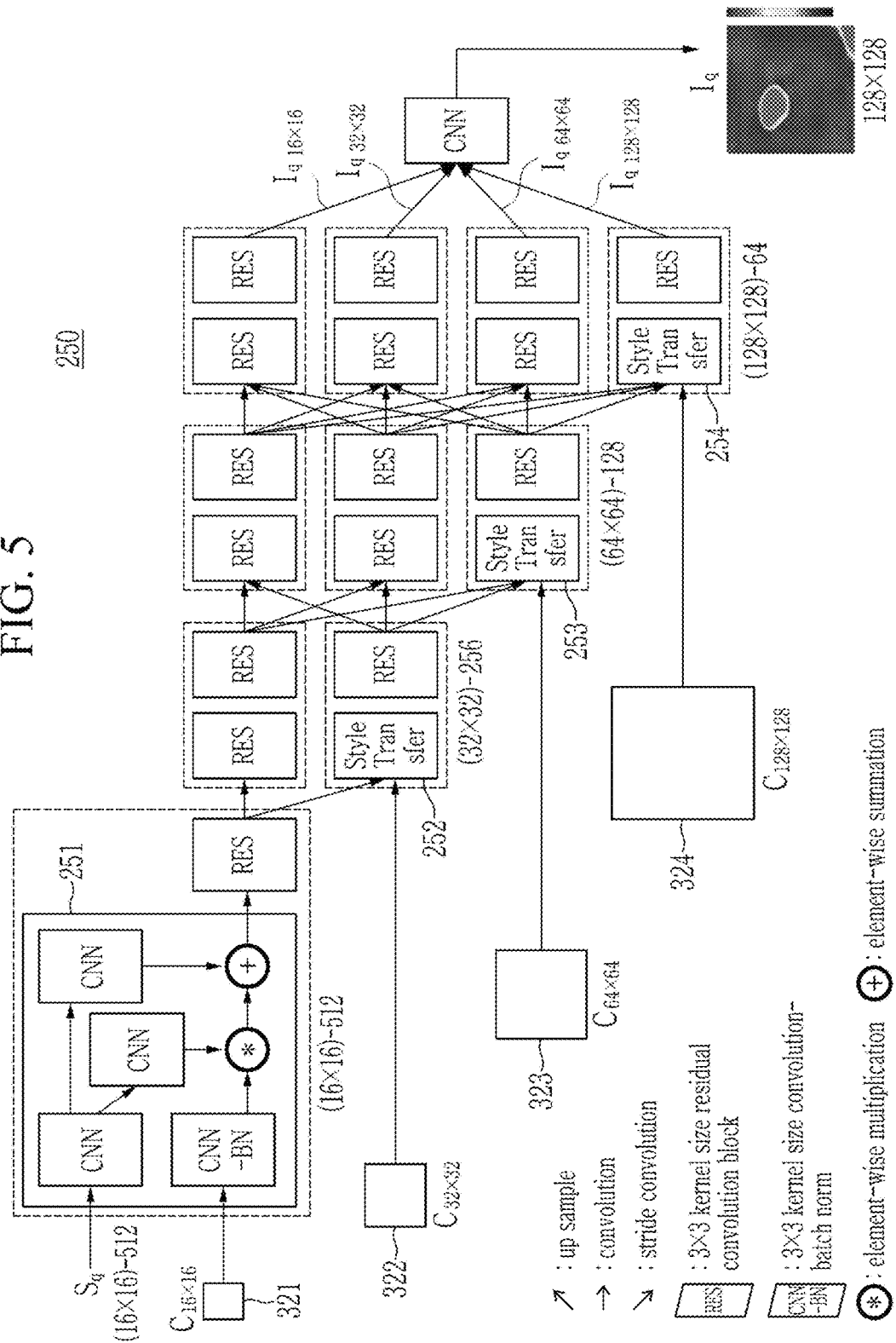
FIG. 5 illustrates a network structure of a decoder according to an exemplary embodiment.

FIG. 3 illustrates a network structure of a style encoder according to an exemplary embodiment, FIG. 4 illustrates a network structure of a B-mode encoder according to an exemplary embodiment, and FIG. 5 illustrates a network structure of a decoder according to an exemplary embodiment.

Referring to FIG. 3, the style encoder 210 may have various network structures that may selectively extract quantitative style features $S_q$ ($S_{SOS}$, $S_{AC}$, $S_{ESC}$, and $S_{ESD}$) of the objective variable q included in the pulse-echo data 300.

For example, the style encoder 210 may include an individual encoding layer 211 that receives and individually filters angle-wise pulse-echo data $U_1$, $U_2$, . . . , $U_7$, and multiple conditional encoding layers 213, 215, 217, and 219 that connect features filtered by the individual encoding layer 211, and encode and conditionally normalize the connected features.

The individual encoding layer 211 may be configured to perform 3×3 kernel size convolution, batch normalization, ReLU, and 1×2 stride downsampling.

The multiple conditional encoding layers 213, 215, 217, and 219 may be sequentially connected, and each conditional encoding layer may be configured to perform convolution and conditional normalization. Each conditional encoding layer may normalize an input x by transferring (scaling and shifting) the input x using $\gamma_q$ and $\beta_q$ selected from the ΓB matrix, according to the objective variable q. Referring to Equation 1, $\gamma_q$ is a scaling value for the objective variable q, and $\beta_q$ is a movement value for the objective variable q.

The last conditional encoding layer 219 outputs the quantitative style feature $S_q$ of the objective variable q. The quantitative style feature $S_q$ may be expressed with a spatial resolution $R^{16 \times 16 \times 512}$.

Referring to FIG. 4, the B-mode encoder 230 may include a B-mode image generator 231 and a convolutional neural network 233.

The B-mode image generator 231 may generate a B-mode image 310 by applying Delay and Sum (DAS) and time gain compensation (TGC) to the pulse-echo data 300.

The convolutional neural network 233 may receive the B-mode image 310 and extract a content feature representing structural information of a tissue of the B-mode image 310. The convolutional neural network 233 may have various network structures, for example, a network structure of a VGG-16 model.

The convolutional neural network 233 may extract multi-resolution content features 321, 322, 323, and 324 from B-mode image 310. The multi-resolution content features 321, 322, 323, and 324 may be expressed as, for example, $C_{16 \times 16}$, $C_{32 \times 32}$, $C_{64 \times 64}$, and $C_{128 \times 128}$. The convolutional neural network 233 may include a convolution layer and a pooling layer, and the convolution layer and the pooling layer may sequentially encode the B-mode image into a lower feature space. Each content feature may be extracted from the convolution layer.

Referring to FIG. 5, the decoder 250 receives the quantitative style feature $S_q$ of the objective variable q extracted from the style encoder 210 and the content feature of the B-mode image extracted from the B-mode encoder 230. The decoder 250 style-transfers the content feature of the B-mode image into quantitative images using the quantitative styling feature $S_q$, and gradually reconstructs the quantitative images generated by the style transfer to output a detailed quantitative image $I_q$ of the objective variable.

The decoder 250 may have a network structure capable of reconstructing a high-resolution quantitative image by gradually synthesizing multi-resolution content features and may include, for example, HRNet based parallel multi-resolution subnetworks.

The decoder 250 may reconstruct quantitative images through the parallel multi-resolution subnetwork. A multi-resolution convolution may preserve low-resolution features while minimizing information loss while integrating various quantitative profiles to generate high-resolution quantitative images. Multi-resolution fusion is implemented in all nodes of subnetworks to exchange information through multi-resolution representation, which plays an important role in extracting high-resolution quantitative images.

In the decoder 250, an arrow pointing to a lower N level shows downsampling, which outputs features in which a width and a height are reduced by 2N times compared to the previous layer, but the number of channels is increased by 2N times. An arrow pointing to an upper N level shows upsampling, which outputs features in which the width and the height are increases by 2N times compared to the previous layer, but the number of channels is reduced by 2N times. For example, the decoder 250 may be constituted by four steps that receive four content features as an input. Each step of the decoder 250 repeats downsampling, upsampling, and integration of the input and outputs quantitative images ($I_{q. 16 \times 16}$, $I_{q. 32 \times 32}$, $I_{q. 64 \times 64}$, $I_{q. 128 \times 128}$) of the corresponding stage in an output subnetwork, and quantitative images may be synthesized via 1×1 convolution.

Each subnetwork may be constituted by, for example, two residual convolution blocks (RES). Meanwhile, the input subnetwork is constituted by a style transfer and a residual convolution block (RES), and may reconstruct a quantitative image after applying quantitative styling features to the input content features.

The style transfer 251 transfers a style by applying the quantitative styling feature $S_q$ to the content feature $C_{16 \times 16}$. The style transfer 251 may style-transfer the content feature into the quantitative image, as shown in Equation 2. The quantitative image generated by style transfer the style transfer 251 is passed to the residual convolution block (RES).

The remaining style transfers 252, 253, and 254 may receive a quantitative image in which the quantitative style features are reflected on the content features from a higher level, and apply the quantitative image to the content features input at the corresponding level to transfer the input into a quantitative style.

Figure 6:
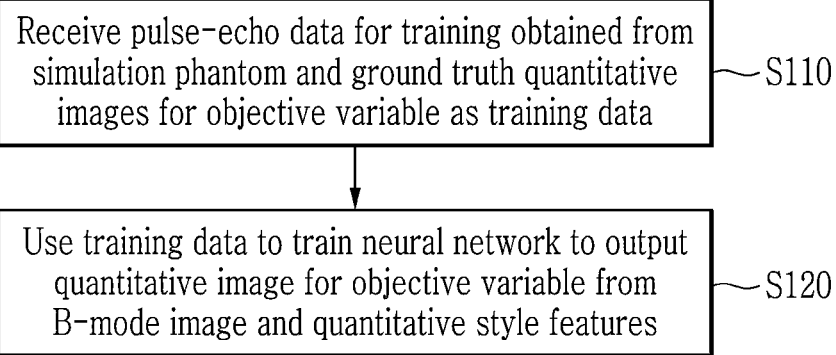
FIG. 6 is a flowchart of a training method of a neural network according to an exemplary embodiment.

FIG. 6 is a flowchart of a training method of a neural network according to an exemplary embodiment.

Referring to FIG. 6, the imaging device 100 receives pulse-echo data for training obtained from a simulation phantom and ground truth quantitative images for the objective variable as training data (S110).

The imaging device 100 uses the training data to train the neural network 200 to output a quantitative image for the objective variable from the B-mode image and the quantitative style features (S120). The imaging device 100 may train the neural network 200 using the objective function shown in Equation 3. The B-mode image may be generated by applying Delay and Sum (DAS) and time gain compensation (TGC) to the pulse-echo data 300. The quantitative style features may be extracted by conditionally encoding pulse-echo data for training according to the objective variable.

Figure 7:
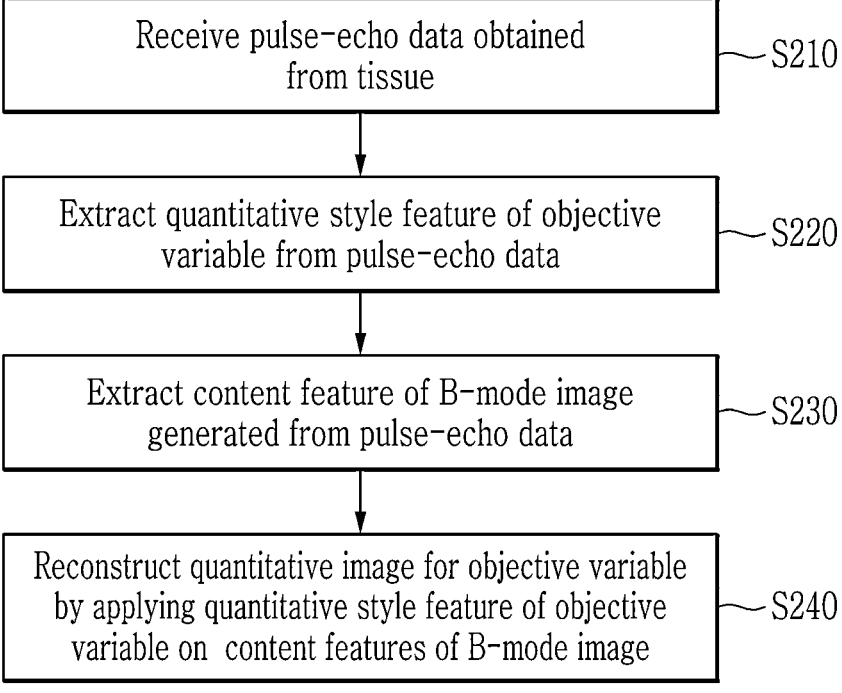
FIG. 7 is a flowchart of a multi-variable quantitative imaging method of a medical ultrasound according to an exemplary embodiment.

FIG. 7 is a flowchart of a multi-variable quantitative imaging method of a medical ultrasound according to an exemplary embodiment.

Referring to FIG. 7, the imaging device 100 receives pulse-echo data obtained from a tissue (S210). The pulse-echo data is RF data obtained for ultrasound signals radiated with different beam patterns.

The imaging device 100 extracts a quantitative style feature of an objective variable from the pulse-echo data (S220). The imaging device 100 may selectively normalize quantitative style information included in the pulse-echo data according to the objective variable q, and extract the quantitative style feature of the objective variable by using the trained style encoder 210.

The imaging device 100 extracts a content feature of a B-mode image generated from the pulse-echo data (S230). The imaging device 100 uses the trained B-mode encoder 230 to generate a B-mode image by Delay and Sum (DAS) and time gain compensation (TGC) to the pulse-echo data, and extract a content feature including tissue structure information of the B-mode image. The imaging device 100 may extract content features at multiple resolutions from the B-mode image.

The imaging device 100 reconstructs a quantitative image for the objective variable by applying the quantitative style feature of the objective variable on the content features of the B-mode image (S240). The imaging device 100 style-transfers the content feature of the B-mode image into quantitative images using the quantitative styling feature, and gradually reconstructs the quantitative images generated by the style transfer to output a detailed quantitative image of the objective variable. The imaging device 100 uses a decoder 250 constituted by HRNet-based parallel multi-resolution subnetworks to style-transfer multi-resolution content features into quantitative images and fuse the quantitative images through parallel convolution to output the detailed quantitative image. The decoder 250 may style-transfer the content feature of the B-mode image into quantitative images through a style transfer.

Figure 8:
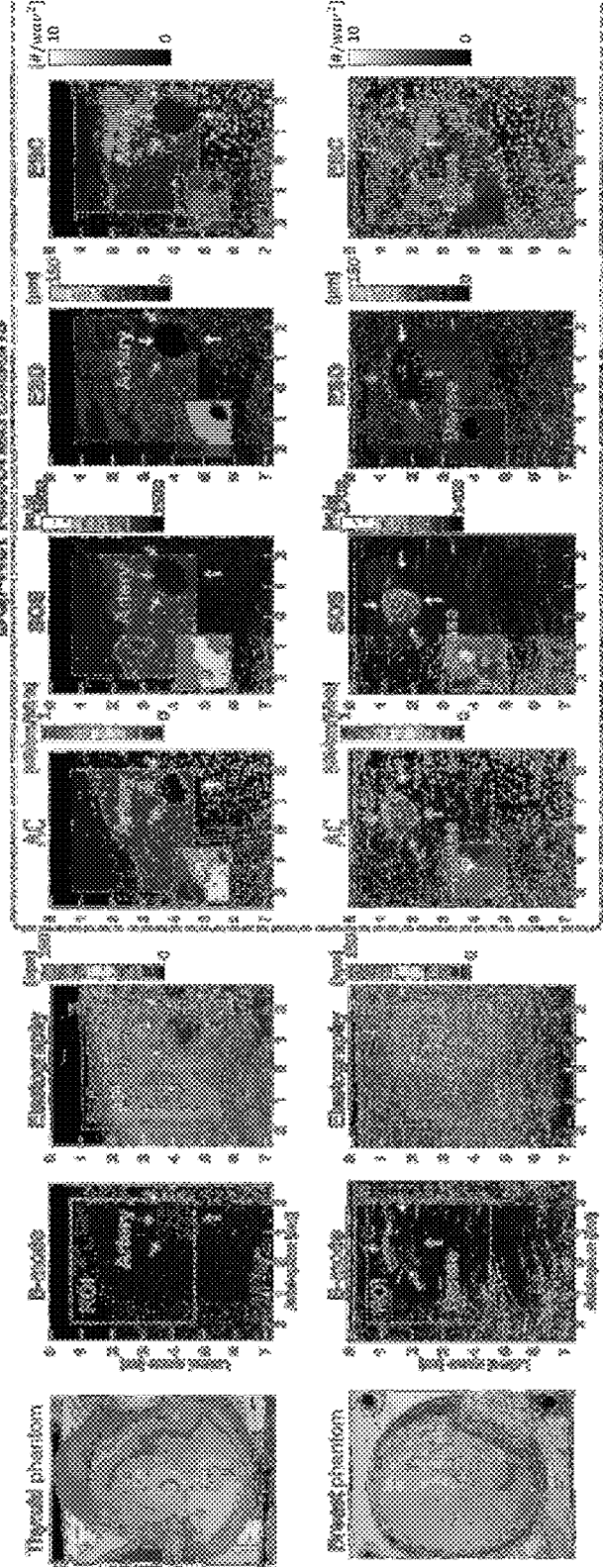
FIG. 8 is a diagram illustrating a multi-variable quantitative imaging result of a biomimetic phantom.
Figure 9:
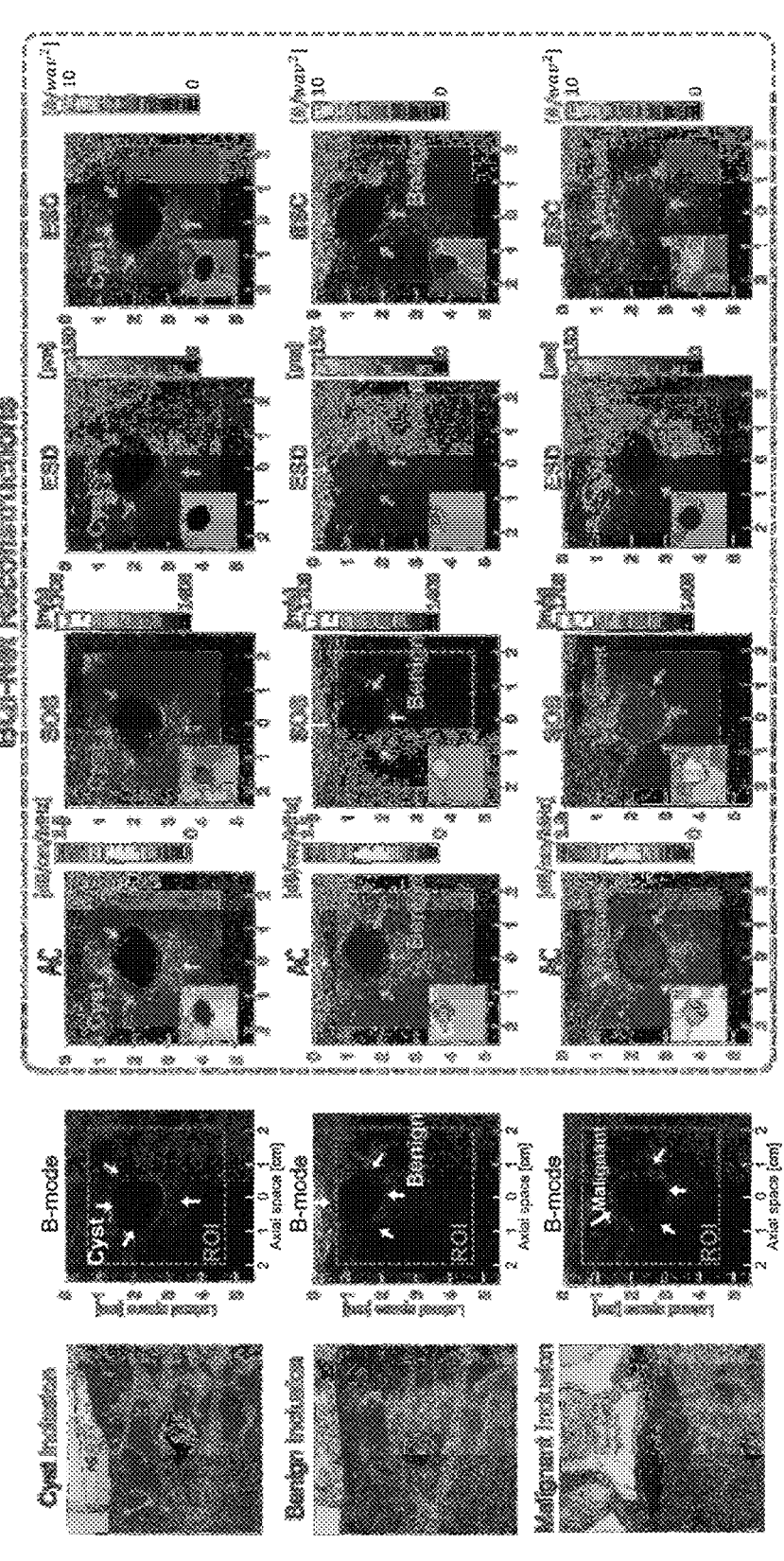
FIG. 9 is a diagram illustrating a multi-variable quantitative imaging result through an ex-vivo experiment.

In this way, the imaging device 100 outputs the quantitative image for the objective variable using a correlation between the B-mode image generated from the pulse-echo data and the quantitative style information extracted from the pulse-echo data. FIG. 8 is a diagram illustrating a multi-variable quantitative imaging result of a biomimetic phantom, and FIG. 9 is a diagram illustrating a multi-variable quantitative imaging result through an ex-vivo experiment.

Referring to FIG. 8, the BQI-Net neural network 200, which extracts quantitative information using structural information of the B-mode image, clearly identifies the artery with the surrounding muscle background in the thyroid phantom. It can be seen that the neural network 200 contains accurate structural information compared to the B-mode image or an image extracted by elastography. Additionally, referring to Table 1, it can be seen that the Speed of Sound (SoS), the Attenuation Coefficient (AC), the Effective Scatterer Concentration (ESC), and the effective scatterer diameter (ESD) reconstructed from the pulse-echo data by the neural network 200 are within a range of a ground truth.

Compared to cystic lesions, benign lesions reconstructed by the BQI-Net neural network 200 exhibit higher AC and SoS of 0.26 dB/cm/MHz and 63 m/s, and errors are less than 2.0% and 1.4%, respectively. This corresponds to an actual biomechanical difference between cystic lesions and benign lesions.

Malignant lesions reconstructed by the BQI-Net neural network 200 exhibit an ESD of 83.8 $\mu$m lower and an ESC of 4.21/wav$^2$ higher than those of benign lesions.

Therefore, lesions may be distinguished based on various quantitative information reconstructed by the BQI-Net neural network 200.

Figure 10:
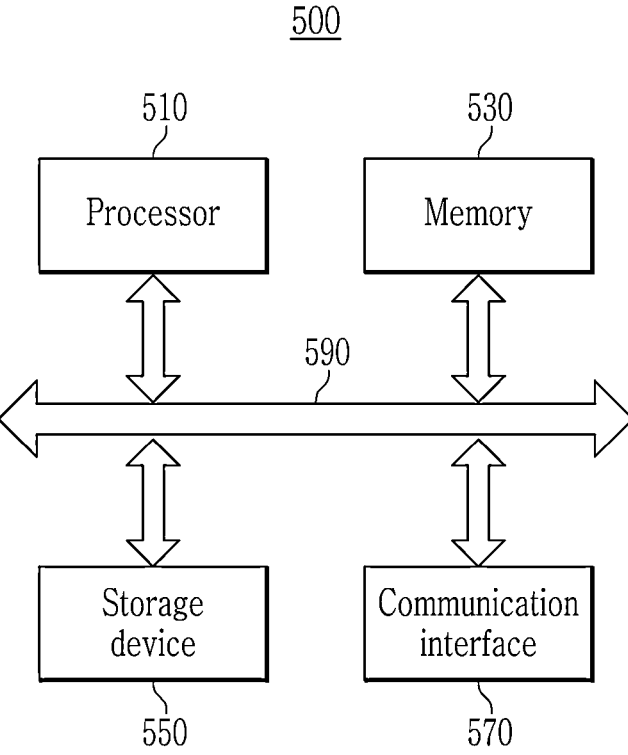
FIG. 10 is a configuration diagram of a computing device according to an exemplary embodiment.

FIG. 10 is a configuration diagram of a computing device according to an exemplary embodiment.

Referring to FIG. 10, the imaging device 100 may be a computing device 500 operated by at least one processor and connected to the ultrasound probe 10 or a device that provides data acquired from the ultrasound probe 10.

The computing device 500 may include one or more processors 510, a memory 530 that loads a program executed by the processor 510, a storage 550 that stores programs and various data, a communication interface 570, and a bus 590 connecting them. Besides, the computing device 500 may further include various components. When loaded to the memory 530, the program may include instructions that cause the processor 510 to perform methods/operations according to various exemplary embodiments of the present disclosure. That is, the processor 510 may perform the methods/operations according to various exemplary embodiments of the present disclosure by executing the instructions. The instructions are a series of computer-readable instructions grouped based on a function and indicate components of the computer program or those that are executed by the processor.

TABLE 1

| | | | AC [dB/cm/MHz] | SoS [m/s] | ESD [μm] | ESC [/wav$^2$] |
|---|---|---|---|---|---|---|
| Thyroid Phantom | Background | Ground Truth | 0.5 ± 0.1 | 1540 ± 10 | 60~100 | N.A (high) |
| | | Reconstruction | 0.43 | 1551 | 62.0 | 3.83 |
| | Artery | Ground Truth | 0.1 ± 0.1 | 1510 ± 10 | 0.00 | 0.00 |
| | | Reconstruction | 0.12 | 1514 | 0.02 | 1.96 |
| Breast Phantom | Background | Ground Truth | 0.3 ± 0.05 | 1475 ± 10 | N.A. (high) | N.A. (low) |
| | | Reconstruction | 0.23 | 1489 | 30.6 | 2.28 |
| | Dense Mass | Ground Truth | 0.54 ± 0.05 | 1610 ± 20 | N.A. (low) | N.A. (high) |
| | | Reconstruction | 0.50 | 1607 | 2.76 | 5.72 |

In the breast phantom for evaluating the ability to distinguish cancer lesions, it can be seen that the BQI-Net neural network 200 accurately classifies the lesion as a dense mass. Additionally, the BQI-Net neural network 200 provides high-contrast attenuation coefficient images and SoS images, despite low acoustic impedance contrast. The neural network 200 may output the Attenuation Coefficient (AC) and the Speed of Sound (SoS) of the lesion with an error of less than 0.04 dB/cm/MHz and 3 m/s. In addition, the ESD and ESC of the lesion extracted from the neural network 200 have lower ESD and higher ESC than the background, showing that the neural network 200 outputs results that are well correlated with the characteristics of the small and dense tumor.

Referring to FIG. 9, in order to confirm that the BQI-Net neural network 200 distinguishes cancer lesions with high specificity, an ex-vivo experiment result using cyst, benign, and malignant lesion tissues is illustrated. Considering malignant cell division and concentration, malignant lesions are constructed to have low ESD and high ESC.

The processor 510 controls the overall operation of each component of the computing device 500. The processor 510 may be configured to include a central processing unit (CPU), a microprocessor unit (MPU), a micro controller unit (MCU), a graphic processing unit (GPU), or any type of processor well-known in a technical field of the present disclosure. Further, the processor 510 may perform an operation of at least application or program for executing the method/operation according to various exemplary embodiments of the present disclosure.

The memory 530 stores various types of data, instructions, and/or information. The memory 530 may load one or more programs from the storage 550 in order to execute the method/operation according to various exemplary embodiments of the present disclosure. The memory 530 will be able to be implemented as a volatile memory such as RAM, but a technical scope of the present disclosure is not limited thereto. The storage 550 may store non-temporarily store the program. The storage 550 may be configured to include a nonvolatile memory such as a read only memory (ROM), an erasable programmable ROM (EPROM), an electrically erasable programmable ROM (EEPROM), a flash memory or the like, a hard disk, a removable disk, or any type of computer-readable recording medium well-known in the art to which the present disclosure pertains.

The communication interface 570 supports wired/wireless communication of the computing device 500. To this end, the communication interface 570 may be configured to include a communication module well-known in the technical field of the present disclosure.

The bus 590 provides a communication function between components of the computing device 500. The bus 590 may be implemented as various types of buses such as an address bus, a data bus, and a control bus.

As described above, according to the exemplary embodiment, multi-variable quantitative images can be reconstructed in real time from ultrasound data of a tissue through a single neural network.

According to the exemplary embodiment, by applying quantitative style information to a B-mode image that provides accurate tissue structure information, various types of clinically important quantitative information can be provided simultaneously and high sensitivity and specificity sufficient to identify and classify cancer lesions can be provided.

According to the exemplary embodiment, since an ultrasound probe and an imaging device for B-mode imaging can be used as they are, image photographing is simple and various organs that can be measured with existing ultrasound imaging equipment can be measured.

According to the exemplary embodiment, a high-quality quantitative image can be reconstructed regardless of the user's skill level using a single ultrasound probe.

The exemplary embodiments of the present disclosure described above are not implemented only through the apparatus and the method and can be implemented through a program which realizes a function corresponding to a configuration of the exemplary embodiments of the present disclosure or a recording medium having the program recorded therein.

While the present disclosure has been described in connection with what is presently considered to be practical exemplary embodiments, it is to be understood that the present disclosure is not limited to the disclosed exemplary embodiments. On the contrary, it is intended to cover various modifications and equivalent arrangements included within the spirit and scope of the appended claims.

The invention claimed is:

1. A method of operating an imaging device, wherein the method is performed by at least one processor, the method comprising:

receiving pulse-echo data obtained from a tissue;

generating a B-mode image from the pulse-echo data;

in response to a selection of an objective variable, extracting a style feature of the objective variable from the pulse-echo data;

generating style-transferred content features by applying the style feature on content features of the B-mode image; and reconstructing a quantitative image of the objective variable using the style-transferred content features, wherein the style feature varies according to the selected objective variable.

2. The method of claim 1, wherein the pulse-echo data is radio frequency (RF) data in which ultrasound signals incident on the tissue with different beam patterns are reflected on the tissue, and returned.

3. The method of claim 1, wherein the objective variable includes at least one of Speed of Sound (SoS), Attenuation Coefficient (AC), Effective Scatterer Concentration (ESC), or effective scatterer diameter (ESD).

4. The method of claim 1, wherein the generating style-transferred content features includes style-transferring the content features of the B-mode image using the style feature to generate the style-transferred contents in form of images.

5. The method of claim 1, wherein the extracting the style feature of the objective variable includes extracting the style feature of the selected objective variable from the pulse-echo data, through conditional encoding according to the selected objective variable.

6. The method of claim 1, wherein the content features of the B-mode image include geometric information of the tissue in the B-mode image.

7. The method of claim 1, wherein the content features of the B-mode image include multi-resolution content features.

8. The method of claim 1, wherein the reconstructing the quantitative image of the objective variable includes generating a high-resolution quantitative image by using parallel multi-resolution subnetworks.

9. The method of claim 1, wherein the extracting the style feature of the objective variable includes:

selecting normalization parameters according to the objective variable; and extracting the style feature of the objective variable from the pulse-echo data by performing normalization using the normalization parameters, wherein the normalization parameters include a scaling value and a shift value that are selected from a matrix according to the objective variable, and wherein the performing normalization using the normalization parameters includes performing conditional instance normalization (CIN) using the scaling value and the shift value.

10. The method of claim 1, wherein the generating style-transferred content features includes performing spatially adaptive demodulation by spatially adaptively transferring each of the content features having a size of W×H into an image having C channels through the styling feature expressed with a spatial resolution $R^{W \times H \times C}$, where W, H, and C are integers.

11. A method of operating an imaging device, wherein the method is performed by at least one processor, the method comprising:

in response to a selection of an objective variable, extracting a style feature of the objective variable included in pulse-echo data by using the style encoder;

generating a B-mode image from the pulse-echo data, and extracting content features of the B-mode image, by using a B-mode encoder; and reconstructing a quantitative image of the objective variable by applying the style feature of the objective variable on content features of the B-mode image, by using a decoder, wherein the style encoder is a neural network trained to extract a style feature of a selected objective variable from the pulse-echo data through conditional encoding according to the selected objective variable, and wherein the style feature varies according to the selected objective variable.

12. The method of claim 11, wherein the B-mode encoder is a neural network trained to generate a B-mode image from the pulse-echo data, and extract the content features from the B-mode image, and wherein the content features include geometric information.

13. The method of claim 11, wherein the decoder is a neural network trained to receive content features extracted from the B-mode encoder, style-transfer the content features of the B-mode image into quantitative images by using the style feature, and reconstruct the quantitative image of the objective variable using the style-transferred content features.

14. The method of claim 13, wherein the decoder is a neural network with a structure of parallel multi-resolution subnetworks.

15. The method of claim 11, wherein the objective variable includes at least one of Speed of Sound (SoS), Attenuation Coefficient (AC), Effective Scatterer Concentration (ESC), or effective scatterer diameter (ESD).

16. An imaging device comprising:

a memory configured to store instructions; and a processor configured to execute the instructions to:

receive pulse-echo data obtained from a tissue;

generate a B-mode image from the pulse-echo data;

in response to a selection of an objective variable, extract a style feature of the objective variable from the pulse-echo data;

generate style-transferred content features by applying the style feature on content features of the B-mode image; and reconstruct a quantitative image of the objective variable using the style-transferred content features, wherein the style feature varies according to the selected objective variable.

17. The imaging device of claim 16, wherein the processor is configured to style-transfer the content features of the B-mode image using the style feature to generate the style-transferred contents in form of images.

18. The imaging device of claim 16, wherein the processor is configured to extract the style feature of the selected objective variable from the pulse-echo data, through conditional encoding according to the selected objective variable.

19. The imaging device of claim 16, wherein the objective variable includes at least one of Speed of Sound (SoS), Attenuation Coefficient (AC), Effective Scatterer Concentration (ESC), or effective scatterer diameter (ESD).

* * * * *